United States Patent [19]

Balhoff et al.

[11] Patent Number: 5,210,304
[45] Date of Patent: May 11, 1993

[54] PROCESS FOR PREPARING HYDROCARBYL AROMATIC AMINES

[75] Inventors: John F. Balhoff; Donald E. Balhoff, both of Baton Rouge, La.

[73] Assignee: Ethyl Corporation, Richmond, Va.

[21] Appl. No.: 667,221

[22] Filed: Mar. 11, 1991

[51] Int. Cl.$^5$ .......................................... C07C 321/28
[52] U.S. Cl. .................................. 564/440; 564/307; 564/335; 546/290; 548/484; 548/541; 548/331.5; 548/326.5
[58] Field of Search ........................ 564/440, 330, 307

[56] References Cited

U.S. PATENT DOCUMENTS 4,324,920  4/1982  McKinnie et al. ................... 568/54
4,670,598  6/1987  Davis ................................. 564/440
4,792,633  12/1988  Wojtkowski ........................ 568/46

Primary Examiner—Glennon H. Hollrah
Assistant Examiner—Shailendra Kumar
Attorney, Agent, or Firm—Richard J. Hammond

[57] ABSTRACT

A continuous process for the hydrocarbylthiation of aromatic amines is disclosed. The process involves forming an admixture of aromatic amine, hydrocarbyl disulfide and an effective amount of a Lewis acid catalyst and subsequently allowing such admixture to flow as a thin film along a column. An inert gas is passed in a counter-current manner through the admixture. The liquid thiohydrocarbyl aromatic amine product is then separated from the gaseous effluent 9 Claims, No Drawings

PROCESS FOR PREPARING HYDROCARBYL AROMATIC AMINES

FIELD OF INVENTION

This invention relates to hydrocarbylthio substituted aromatic amines and more particularly to a process for preparing them.

BACKGROUND

As disclosed in U.S. Pat. No. 4,594,453 (Ranken et al.), it is known that various (hydrocarbylthio)aromatic amines are useful as intermediates in the preparation of biologically-active materials, polyurethanes, etc.; and they can be prepared by reacting an aromatic amine with an alkyl disulfide in the presence of a catalytic amount of a Lewis acid. The preferred catalysts of Ranken et al. are metal halides, such as aluminum chloride, boron trifluoride, boron trichloride, ferric chloride, and zinc chloride.

In the case of at least some aromatic amines, it has been found that the preferred catalysts identified by Ranken et al. have the disadvantages of effecting the desired hydrocarbylthiations at too slow a rate to be completely satisfactory and of sometimes providing too low a yield of product.

In U.S. Pat. No. 4,751,330 (Davis), various alkylthioaromatic amines are prepared by reacting an aromatic amine with an alkyl disulfide in the presence of a metal or metal halide catalyst and iodine as a promoter. These reactions are noted to have higher reaction rates and/or higher yields than the prior art reactions discussed above.

However, even the improved process of Davis requires many hours to achieve satisfactory yields.

SUMMARY OF INVENTION

An object of this invention is to provide a novel continuous process for preparing hydrocarbylthio substituted aromatic amines.

Another object is to provide such a process wherein the products are prepared by the hydrocarbylthiation of aromatic amines in the presence of metal or metal halide catalysts.

A further object is to provide such a process wherein the reaction rates and/or product yields are improved.

These and other objects are attained by reacting an aromatic amine with a hydrocarbyl disulfide in the presence of a catalytic amount of a metal or metal halide in a packed bed reactor where gaseous hydrocarbyl disulfide is allowed to flow through the liquid admixture of amine, catalyst and hydrocarbyl disulfide.

DETAILED DESCRIPTION OF THE PREFERRED EMBODIMENTS

Aromatic amines utilizable in the practice of the invention include (1) compounds having at least one amino group attached to a carbocyclic or heterocyclic ring of an aromatic compound containing one or more simple and/or fused rings, such as benzene, naphthalene, anthracene, pyrrole, pyridine, indole, etc., rings and (2) reactive heterocyclic amines, such as pyrrole, indole, imidazole, etc. The compounds may bear no substituents other than the required amino group, or they may bear substituents inert to the reaction conditions, such as one or more additional amino groups or substituents such as chloro, fluoro, alkyl, aryl, alkaryl, or aralkyl groups on any positions other than those to be substituted by hydrocarbylthio groups. In the case of coupled aromatic rings, the rings may be directly attached to one another or may be coupled through a bridge such as an oxygen, sulfur, sulfoxide, sulfone, alkyl, or another hydrocarbon link. Useful compounds include, e.g., 4,4'-methylenedianiline, 4-(phenylthio)aniline, 1,3-dimethylpyrrole, 1-methylpyrrole, 2-aminobiphenyl, 4-phenoxyaniline, 7-methylindole, aminobenzenes containing one or two amino groups, such as aniline, 4-butylaniline, 4-methylaniline, 4-chloroaniline, 2-ethylaniline, N-methylaniline, 2,4- and 2,6-diaminotoluenes or mixtures of such toluenes, 2,6-diamino-1-ethylbenzene, 2,4-diaminoxylenes, 2,6-diaminoxylenes or mixtures of such isomers, etc.

Hydrocarbyl disulfides which ma be reacted with the aromatic amines include saturated and unsaturated aliphatic, cycloaliphatic, and aromatic disulfides in which the alkyl groups optionally bear inert, such as chloro, substituents. Exemplary of such compounds are methyl, ethyl, propyl, n-butyl, sec-butyl, t-butyl, 2-chloropentyl, cyclopentyl, cyclohexyl, phenyl, benzyl, p-tolyl, and p-chlorophenyl disulfides, etc.

The reaction of the aromatic amine with the hydrocarbyl disulfide is generally conducted at a temperature in the range of about 20°–300° C. and at a pressure of atmospheric up to about 1000 psi in the presence of a catalyst. Suitable catalysts are Lewis acid catalysts, such as metal halides, e.g., aluminum chloride, boron trifluoride, ferric chloride, zinc chloride, copper iodide, etc.; and the organometallic compounds derived from the reaction of the aromatic amine with the metal halides, metal alkyls, and reactive metals such as aluminum. The preferred catalysts are the metal halides, such as copper (I) iodide, aluminum chloride, boron trifluoride, and boron trichloride. Copper iodide (I) is especially preferred. The catalyst is employed in catalytic amounts, generally in a catalyst/aromatic amine mole ratio of about 0.01–0.5/1, preferably about 0.01–0.2/1. When the catalyst is one of the more active catalysts and/or is used in a relatively large amount, the temperature and pressure conditions required are milder than when a less active catalyst and/or a lesser amount of catalyst is utilized. Thus, e.g., when about 0.01–0.1 molar proportion of aluminum chloride is employed, particularly satisfactory results are obtained when the reaction is conducted at about 100°–50° C. and atmospheric pressure, whereas higher temperatures and/or elevated pressures are required for comparable results when aluminum is used instead of aluminum chloride.

In conducting the continuous process of the present invention, it has been discovered that when a heated mixture of catalyst, aromatic amine and hydrocarbyl disulfide is allowed to flow as a thin film along a column and an inert (nonreactive) gas is permitted to flow through the moving liquid film mixture in a countercurrent manner, the reaction time to produce the desired hydrocarbylthio substituted aromatic amine product is dramatically decreased in comparison to the conventional batch process where the ingredients are admixed and allowed to react in a reaction vessel. The inert (nonreactive) gas may be nitrogen, carbon dioxide or the like. Most preferably the inert (non-reactive) gas is gaseous hydrocarbyl disulfide. Reaction times are reduced to a few seconds, i.e., as little as five seconds is necessary to achieve the desired reaction. As the liquid stream emerges from the column, it is comprised principally of monohydrocarbylthio substituted aromatic amine, catalyst residue, and small amounts of unreacted hydrocarbyl disulfide and aromatic amine. Distillation readily separates the hydrocarbylthiolated product from the remainder of the product stream.

The reactant mixture is formed into a thin film by allowing it to flow along the surface of a column. The column is typically packed with granular solids, ceramic plates, screening, etc. in order to facilitate the formation of the thin reactant film.

While it is preferred that inert, granular particles are used in the column, i.e., sand, glass beads, alumina, it has been found that glass beads are most preferably employed for such packing.

The process of the invention results in the formation of alkyl aromatic amines which are useful as intermediates in the preparation of biologically-active materials, polyurethanes, etc. Some of these amines are novel compounds, e.g., those corresponding to the formulas:

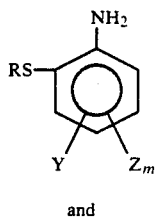

and

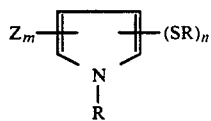

wherein R is an alkyl group; Y is an alkylthio group, Z is an inert substituent, i.e., a substituent which is inert to the reaction conditions, such as chloro, fluoro, nitro, amino, hydrocarbyl, or hydrocarbylthio; m has a value of 0-3; and n is an integer of 2-4. The hydrocarbyl groups are preferably alkyl, e.g., methyl, ethyl, etc., groups.

The following examples are given to illustrate the invention and are not intended as any limitation thereof.

EXAMPLES

Example A

A solution of 3.75 wt % of cuprous iodide (CuI) and 96.25 wt % of commercial toluenediamine (c-TDA)—a material containing 80% 2,4-diaminotoluene and 20% 2,6-diaminotoluene was fed downward at a rate of 2.3 g/min. to a 1" diameter, 11" long stainless steel column with 0.16" Pro-Pak ® packing. Gaseous dimethyl disulfide (DMDS) was fed upward to the column at a rate of 15.7 g/min. DMDS was refluxed back to the column by a water-cooled dephlegmator. The column temperature was maintained at 150° C. with a heating oil jacket. By-product methyl mercaptan was vented to atmosphere and burned by a Bunsen Burner through a Grove back pressure regulator which maintained the column pressure at 28 psig. The effluent was analyzed by gas chromatography and contained 29.1 area% c-TDA, 54.8 area% mono(methylthio) derivatives of c-TDA (MMTDA), 16.1 area% di(methylthio) derivatives of c-TDA (DMTDA).

Example 8

A series of experiments were carried out using partially converted reaction crude as the feed to the column, described in Example A. The reaction crude was prepared by reacting the c-TDA and CuI solution with 50% excess DMDS in a batch reactor at 140° C. and atmospheric pressure. This reaction crude and DMDS were then fed to the column. The resulting effluent was then analyzed by gas chromatography. The feed and effluent compositions are listed in Table I.

TABLE I

| Temp. (°C.) | Pressure (psig) | Crude (g/min) | DMDS | | c-TDA | MMTDA | DMTDA | TMTDA* |
|---|---|---|---|---|---|---|---|---|
| | | | | | | | (area %) | |
| 158 | 28 | 2.4 | 14.9 | in | 26.5 | 59.2 | 14.3 | 0.0 |
| | | | | out | 7.5 | 47.4 | 45.1 | 0.0 |
| 156 | 28 | 2.4 | 14.6 | in | 6.1 | 38.3 | 55.6 | 0.0 |
| | | | | out | 1.5 | 30.2 | 68.1 | 0.2 |
| 158 | 28 | 2.4 | 14.4 | in | 1.2 | 24.2 | 74.4 | 0.2 |
| | | | | out | 0.3 | 12.7 | 86.5 | 0.4 |
| 154 | 28 | 2.7 | 14.2 | in | 0.4 | 13.0 | 86.2 | 0.4 |
| | | | | out | 0.0 | 6.6 | 92.9 | 0.5 |
| 152 | 28 | 2.4 | 14.1 | in | 0.0 | 8.5 | 91.0 | 0.5 |
| | | | | out | 0.0 | 4.0 | 95.3 | 0.7 |

*tri(methylthio) derivatives of c-TDA

Comparative Example A

A suitable reaction vessel was charged with one molar proportion of aniline and 0.067 molar proportion of aluminum chloride. After the reaction mixture had been stirred in a nitrogen atmosphere at 150° C. for 30 minutes and cooled to 100° C., one molar proportion of methyl disulfide was added. The reaction mixture was then stirred and heated at an initial reflux temperature of 130° C. to a final temperature of 170° C. in 25 hours to provide a crude reaction product which was cooled, worked up, and analyzed by gas chromatography, using n-undecane as an internal standard. The analysis showed that the reaction mixture contained 14 wt % methyl disulfide, 19 wt % aniline, 18 wt % 2-(methylthio)aniline, 33 wt % 4-(methylthio)aniline, and 7 wt % 2,4-di(methylthio)aniline.

Comparative Example B

Comparative Example A was essentially repeated except that 0.0085 molar proportion of iodine was added to the initial reaction mixture, and the reflux time required was only 7 hours instead of 25 hours. The reaction resulted in the formation of a reaction mixture containing 12 wt % methyl disulfide, 16 wt % aniline, 17.5 wt % 2-(methylthio)aniline), 37 wt % 4-(methylthio)aniline, and 11.2 wt % 2,4-di(methylthio)aniline.

Comparative Example C

One molar proportion of commercial toluenediamine (c-TDA) a material containing 80% 2,4-diaminotoluene and 20% 2,6-diaminotoluene was heated with 0.065 molar proportion of aluminum chloride at 150° C. for one hour. Methyl disulfide was then added in sufficient excess to maintain the reaction temperature at 135° C., and the reaction was conducted for 39 hours to achieve 100% conversion of the c-TDA. Analysis of the product showed it to contain 16 mole% mono(methylthio) derivatives of c-TDA (MMTDA), 78 mole% di(methylthio) derivatives of c-TDA (DMTDA, and 6 mole% by-products.

Comparative Example D

Comparative Example B was essentially repeated except that the initial reaction mixture contained one molar proportion of c-TDA, 0.068 molar proportion of aluminum chloride, and 0.0032 molar proportion of iodine, and the reaction time required to reach 100% conversion was only 22 hours. The product contained 10 mole% MMTDA, 83 mole% DMTDA, and 6 mole% by-products.

We claim:

1. A continuous process for hydrocarbylthiation of aromatic amines which comprises: (i) passing a thin film feed stream comprising a hydrocarbyl disulfide, hydrocarbyl aromatic amine substituted by halogen and a catalytically effective amount of a metal halide selected from the group consisting of aluminum chloride, boron trifluoride, boron trichloride, ferric chloride, zinc chloride and copper(I) iodide along a column and countercurrently introducing into said thin film feed stream an inert gas; and (ii) separating a hydrocarbylthiol as a gaseous effluent and a liquid hydrocarbylthiolated aromatic amine.

2. The process of claim 1 wherein said aromatic amine is an aminobenzene.

3. The process according to claim 2 wherein said aromatic amine is aniline.

4. The process according to claim 1 wherein said aromatic amine is a diamino toluene.

5. The process according to claim 4 wherein said aromatic amine is a mixture of 2,4-diaminotoluene and 2,6-diaminotoluene.

6. The process according to claim 4 wherein said aromatic amine is a mixture of 2,4-diaminoxylene and 2,6-diaminoxylene.

7. A continuous process for the reaction of methyldisulfide with a mixture of 2,4-diaminotoluene and 2,6-diaminotoluene which comprises: (i) passing a thin film feed stream comprising dimethyl disulfide, an aromatic amine that is a mixture of 2,4-diaminotoluene and 2,6-diaminotoluene and a catalytically effective amount of copper(I) iodide along a column and countercurrently introducing into said thin film feed stream gaseous dimethyl disulfide; and (ii) separating gaseous methyl mercaptan as effluent and a liquid mixture of mono(methylthio)analines and di(methylthio)aniline.

8. The continuous process according to claim 7 wherein said mono(methylthio)aniline is a mixture of 2-(methylthio)aniline and 4-(methylthio)aniline.

9. The continuous process according to claim 7 wherein said thin film feed stream is formed by first admixing in a batch reaction said mixture of 2,4-diaminotoluene and 2,6-diaminotoluene, with dimethyl disulfide in the presence of a catalytically effective amount of copper(I) iodide and then employing said admixture in said continuous process.

* * * * *